(12) United States Patent
Gale et al.

(10) Patent No.: US 8,099,849 B2
(45) Date of Patent: Jan. 24, 2012

(54) OPTIMIZING FRACTURE TOUGHNESS OF POLYMERIC STENT

(75) Inventors: David Gale, San Jose, CA (US); Bin Huang, Pleasanton, CA (US); Vincent Gueriguian, San Francisco, CA (US); Syed Hossainy, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 997 days.

(21) Appl. No.: 11/639,079

(22) Filed: Dec. 13, 2006

(65) Prior Publication Data

US 2008/0147164 A1 Jun. 19, 2008

(51) Int. Cl.
*A61F 2/06* (2006.01)

(52) U.S. Cl. ......... 29/407.05; 29/505; 29/508; 29/522.1

(58) Field of Classification Search .................... 29/454, 29/505, 508, 527.1, 557, 515, 522.1, 407.05, 29/407.08

See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |

(Continued)

FOREIGN PATENT DOCUMENTS

DE 44 07 079 9/1994

(Continued)

OTHER PUBLICATIONS

U.S. Appl. No. 10/317,435, filed Dec. 11, 2002, Hossainy et al.

(Continued)

*Primary Examiner* — David Bryant
*Assistant Examiner* — Christopher Besler
(74) *Attorney, Agent, or Firm* — Squire, Sander & Dempsey (US) LLP

(57) ABSTRACT

Disclosed herein is a method of fabricating a stent assembly comprising radially expanding a polymeric tube to an optimal degree of radial expansion; fabricating a stent from the expanded polymeric tube; and crimping the stent onto a catheter assembly, wherein the temperature of the stent during crimping is an optimal crimping temperature, wherein the optimal degree of radial expansion and the optimal crimping temperature correspond to an optimal fracture toughness exhibited by the crimped stent upon its deployment as a function of degree of radial expansion and crimping temperature.

8 Claims, 2 Drawing Sheets

U.S. PATENT DOCUMENTS

| | | |
|---|---|---|
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |

| | | |
|---|---|---|
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 4,776,337 A | 12/2000 | Palmaz |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 6,878,758 B2 * | 4/2005 | Martin et al. ................. 523/124 |
| 7,335,226 B2 * | 2/2008 | Igaki ............................ 623/1.15 |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0065355 A1 | 4/2003 | Weber |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236563 A1 | 12/2003 | Fifer |
| 2004/0093077 A1 | 5/2004 | White et al. |
| 2004/0098095 A1 | 5/2004 | Burnside et al. |
| 2004/0111149 A1 | 6/2004 | Stinson |
| 2004/0127970 A1 | 7/2004 | Saunders et al. |
| 2004/0143317 A1 | 7/2004 | Stinson et al. |
| 2004/0167610 A1 | 8/2004 | Fleming, III |
| 2004/0181271 A1 | 9/2004 | DeSimone et al. |
| 2005/0119720 A1 * | 6/2005 | Gale et al. ..................... 623/1.11 |
| 2006/0020330 A1 * | 1/2006 | Huang et al. ................. 623/1.49 |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |

| | | |
|---|---|---|
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |

OTHER PUBLICATIONS

Acquarulo et al., *Enhancing Medical Device Performance with Nanocomposite Poly*, Med. Device Link, www.devicelink.com/grabber.php3?URL downloaded Mar. 26, 2007, 4 pgs.

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules, vol. 2, pp. 430-441 (2001).

Hahn et al., *Biocompatibility of Glow-Discharge-Polymerized Films and Vacuum-Deposited Parylene*, J Applied Polymer Sci, vol. 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

Kelley et al., *Totally Resorbable High-Strength Composite Material*, Advances in Biomedical Polymers, vol. 35, pp. 75-85 (1987).

Kubies et al., *Microdomain Structure In polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

NanoComposix, products, www.nanocomposix.com, dowhloaded Mar. 26, 2007, 2 pgs.

Nanosiliver, Photocatalyst and Nanocomposite Material, http://eng.nanocomposite.net downloaded Mar. 26, 2007, 1 pg.

Nichols et al., *Electrical Insulation of Implantable Devices by Composite Polymer Coatings*, ISA Transactions, vol. 26(4), pp. 15-18 (1987).

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants — practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

Tamai et al., *Initial and 6-Month Results of Biodegradable Poly-I-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

Van Vlack, *Elements of Materials Science and Engineering*, Addison-Wesley Publishing Co. (1989), title page, pp. 270-271.

Völkel et al., *Targeting of immunoliposomes to endothelial cells using a single-chain Fv fragment directed against human endoglin (CD105)*, Biochimica et Biophysica Acta 1663, pp. 158-166 (2004).

von Recum et al., *Degradation of polydispersed poly(L-lactic acid) to modulate lactic acid release*, Biomaterials, vol. 16, pp. 441-445 (1995).

Yau et al., Modern Size-Exclusion Liquid Chromatography, Wiley-Interscience Publication, IX-XV (1979).

* cited by examiner

OPTIMIZING FRACTURE TOUGHNESS OF POLYMERIC STENT

BACKGROUND OF THE INVENTION

1. Field of the Invention

This invention relates to a degradable polymeric implantable medical device. Specifically, this invention relates to a method of fabricating a stent.

2. Description of the State of the Art

This invention relates generally to implantable medical devices having a range of mechanical and therapeutic requirements during use. In particular, the invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty. "Restenosis" refers to the reoccurrence of stenosis in a blood vessel or heart valve after it has been subjected to angioplasty or valvuloplasty.

The treatment of a diseased site or lesion with a stent involves both delivery and deployment of the stent. "Delivery" refers to introducing and transporting the stent through a bodily lumen to the treatment site in a vessel. "Deployment" corresponds to the expanding of the stent within the lumen at the treatment site. Delivery and deployment of a stent are accomplished by positioning the stent at one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be, withdrawn allowing the stent to self-expand.

In many treatment applications, the presence of a stent in a body may be necessary for a limited period of time until its intended function of, for example, maintaining vascular patency and/or drug delivery is accomplished. Thus, stents are often fabricated from biodegradable, bioabsorbable, and/or bioerodable materials such that they completely erode only after the clinical need for them has ended.

A stent is typically composed of scaffolding that includes a pattern or network of interconnecting structural elements or struts. The scaffolding is designed to allow the stent to be radially expandable. The pattern is generally designed to maintain the longitudinal flexibility and radial rigidity required of the stent. Longitudinal flexibility facilitates delivery of the stent and radial rigidity is needed to hold open a bodily lumen. A medicated stent may be fabricated by coating the surface of either a metallic or polymeric scaffolding with a polymeric carrier that includes a bioactive agent. The polymeric scaffolding may also serve as a carrier of a bioactive agent.

A stent must be able to satisfy several mechanical requirements. First, the stent must be capable of withstanding the structural loads, namely radial compressive forces, imposed on the stent as it supports the walls of a vessel lumen. This requires a sufficient degree of strength and rigidity or stiffness. In addition to having adequate radial strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion which typically requires substantial deformation of portions of the stent. Once expanded, the stent must maintain its size and shape throughout its service life despite the various forces that may come to bear thereon, including the cyclic loading induced by the beating heart. Therefore, a stent must be capable of exhibiting relatively high toughness which corresponds to high strength and rigidity, as well as flexibility.

Unfortunately, many polymers used for stent scaffoldings and coatings are relatively brittle under physiological conditions, e.g., at body temperature. Many polymers remain relatively brittle, and hence susceptible to mechanical instability such as fracturing while in the body.

SUMMARY

Disclosed herein is a method of fabricating a stent assembly comprising radially expanding a polymeric tube to an optimal degree of radial expansion; fabricating a stent from the expanded polymeric tube; and crimping the stent onto a catheter assembly, wherein the temperature of the stent during crimping is an optimal crimping temperature, wherein the optimal degree of radial expansion and the optimal crimping temperature correspond to an optimal fracture toughness exhibited by the crimped stent upon its deployment as a function of degree of radial expansion and crimping temperature.

Also disclosed herein is a stent assembly comprising: a radially expandable polymeric stent crimped onto a catheter assembly, the stent being fabricated from a radially expanded polymeric tube having an optimal degree of radial expansion, the stent being crimped at an optimal crimping temperature, wherein the optimal degree of radial expansion and the optimal crimping temperature correspond to an optimal fracture toughness exhibited by the crimped stent upon its deployment as a function of the degree of radial expansion and crimping temperature.

Also disclosed herein is a method of fabricating a stent assembly including a stent mounted on a catheter, comprising: determining an optimal degree of radial expansion of a polymeric tube for use in fabricating a stent and an optimal crimping temperature corresponding to an optimal fracture toughness exhibited by the crimped stent upon its deployment as a function of degree of radial expansion and crimping temperature, wherein the optimal fracture toughness is determined by a maximum fracture toughness observed upon deployment of a plurality of stents as a function of degree of radial expansion and crimping temperature, the plurality of stents fabricated from a plurality of polymeric tubes, the plurality of polymeric tubes having two or more different degrees of radial expansion, the plurality of fabricated stents being crimped at two or more different temperatures.

DETAILED DESCRIPTION

Figure 1:
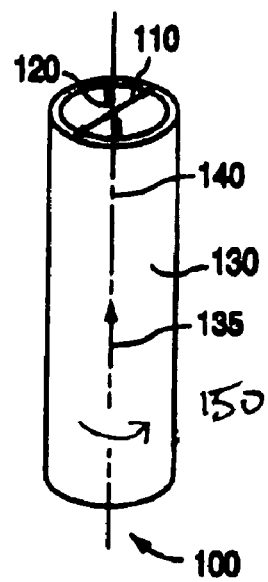
FIG. 1 depicts a stent made up of struts.

Various embodiments of the present invention relate to implantable medical devices configured to have particular mechanical properties such as strength and flexibility. The device as a whole may have desirable properties by controlling the degree of radial expansion and crimping temperature. Therefore, desirable mechanical and/or degradation properties in an implantable medical device may be obtained by controlling the degree of radial expansion and crimping temperature during fabrication of the stent.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). Compressive stress is a normal component of stress applied to materials resulting in their compaction (decrease in length).

"Toughness" is the amount of energy absorbed prior to fracture, or equivalently, the amount of work required to fracture a material. One measure of toughness is the area under a stress-strain curve from zero strain to the strain at fracture. The units of toughness are energy per unit volume of material. See, e.g., L. H. Van Vlack, "Elements of Materials Science and Engineering," pp. 270-271, Addison-Wesley (Reading, Pa., 1989).

A brittle material is a relatively stiff or rigid material that exhibits little or no plastic deformation. As stress is applied to a brittle material, it tends to fracture at a stress approximately equal to its ultimate strength, undergoing little or no plastic deformation in the process. A polymer below its $T_g$ tends to be brittle. In contrast, a ductile material under an applied stress exhibits both elastic and plastic deformation prior to fracture. Above its $T_g$, a polymer is ductile.

A fracture may be categorized as either ductile or brittle. A relatively low amount of energy is required to fracture brittle materials. Conversely, ductile materials can absorb a relatively high amount of energy prior to fracture. Therefore, ductile materials tend to exhibit a higher toughness than brittle materials. Toughness is a desirable characteristic in implantable medical devices.

Many biodegradable polymers suitable for use as a stent scaffolding and/or a coating are relatively brittle under physiological conditions. This is particularly true for biodegradable polymers with a $T_g$ above a body temperature, such as poly (L-lactide). Therefore, for such polymers that are brittle under physiological conditions, the fracture toughness is lower than desirable in implantable medical devices. Various embodiments of the present invention relate to increasing the fracture toughness of a polymer for use in an implantable medical device.

As mentioned above, a polymeric stent must be able to satisfy a number of mechanical requirements. First, the stent must withstand structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure.

Some embodiments of manufacturing a stent include fabricating the stent from a polymer conduit or tube. The tube may be cylindrical or substantially cylindrical in shape. For example, FIG. 1 depicts a tube 100. Tube 100 is a cylinder with an outside diameter 110 and an inside diameter 120. FIG. 1 also depicts an outside surface 130 and a cylindrical axis 140 of tube 100. When referred to below, unless otherwise specified, the "diameter" of the tube refers to the outside diameter of tube 100.

Figure 2:
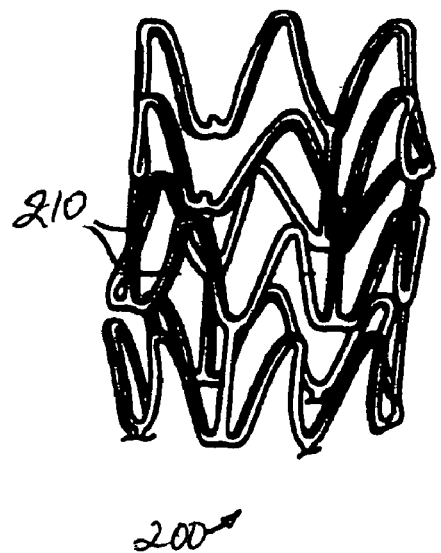
FIG. 2 is a polymeric tube for use in fabricating a stent.

A stent can be fabricated from a tube by laser cutting a pattern on the tube. Representative examples of lasers that may be used include laser types such as excimer, carbon dioxide, and YAG. Chemical etching may also be used to form a pattern on the elongated tube. FIG. 2 depicts a three-dimensional view of a stent 200 which may be formed from tube 100 in FIG. 1. As depicted in FIG. 2, the structure of a stent is typically composed of a scaffolding that includes a pattern or network of interconnecting structural elements often referred to in the art as struts 210 or bar arms. The pattern is not limited to the depicted stent pattern. The scaffolding is designed so that the stent can be radially compressed (to allow crimping) and radially expanded (to allow deployment). A conventional stent is allowed to expand and contract through movement of individual structural elements of a pattern with respect to each other.

The struts or bar arms of polymeric stents are susceptible to cracking during crimping and deployment due to inadequate toughness of the polymer. The localized portions of the stent pattern subjected to substantial deformation tend to be the most vulnerable to failure.

Disclosed herein are embodiments of a method for fabricating a stent that has increased fracture toughness. The mechanical properties of the polymeric tube used to make the stent are modified by the radial expansion of the tube. Stress is applied to the polymer during radial expansion that induces molecular orientation along the direction of stress. Mechanical properties along the direction of applied stress are modified. For example, strength, modulus, and toughness are some of the important properties that can be modified by radial expansion since these properties depend upon orientation of polymer chains in a polymer. Molecular orientation refers to the relative orientation of polymer chains along a longitudinal or covalent axis of the polymer chains.

Due to the magnitude and directions of stresses imposed on a stent during use, it is important for the mechanical stability of the stent to have suitable mechanical properties, such as strength and modulus, in the axial and circumferential directions. Therefore, by modifying the mechanical properties of a tube to be used in the fabrication of a stent, orientation is induced from applied stress in the axial direction, circumferential direction, or both. Thus, a modified tube can have a desired degree of orientation in both directions, which is known as biaxial orientation.

Polymer tubes formed by extrusion methods tend to possess a significant degree of axial polymer chain alignment. However, such conventionally extruded tubes tend to possess no or substantially no polymer chain alignment in the circumferential direction. A tube made from injection molding has a relatively low degree of polymer chain alignment in both the axial and circumferential directions.

Since highly oriented regions in polymers tend to be associated with higher strength and modulus, it may be desirable to incorporate processes that induce alignment of polymer chains along one or more preferred axes or directions into fabricating of stents. Additionally, it is believed that the toughness of the polymer stent can also be increased through radial expansion.

Therefore, it can be desirable to fabricate a stent from a polymeric tube not only with induced orientation in the axial direction, as shown by an arrow 135 in FIG. 1, but also in the circumferential direction as indicated by an arrow 150. In this way, a biaxial oriented tube may be configured to have desired strength and modulus in both the axial direction as well as the circumferential direction, as well as increased toughness.

The degree of radial expansion, and thus induced radial orientation and strength, of a tube can be quantified by a radial expansion (RE) ratio:

Outside Diameter of Expanded Tube/Original Inside Diameter of Tube

The RE ratio can also be expressed as a percent expansion:

% Radial expansion=(RE ratio−1)×100%

In an exemplary embodiment, the stent can be fabricated from a tube consisting essentially of PLLA. In some embodiments, a tube can be expanded to at least 100%, 300%, 500%, 600%, 700%, or greater than 700%.

In one embodiment, the tube may be radially expanded by blow molding. In some embodiments, a polymer tube for fabrication of an implantable medical device may be radially expanded by increasing a pressure in a polymer tube, for example, by conveying a fluid into the tube. The polymer tube may be deformed axially by applying a tensile force by a tension source at one end while holding the other end stationary. Alternatively, a tensile force may be applied at both ends of the tube.

In some embodiments, blow molding may include first positioning a tube in an annular member or mold. The mold may act to control the degree of radial deformation of the tube by limiting the deformation of the outside diameter or surface of the tube to the inside diameter of the mold. The inside diameter of the mold may correspond to a diameter less than or equal to a desired diameter of the polymer tube. Alternatively, the fluid temperature and pressure may be used to control the degree of radial expansion by limiting deformation of the inside diameter of the tube as an alternative to or in combination with using the mold.

As indicated above, the polymer tube may also be heated prior to, during, and subsequent to the deformation. In one embodiment, the tube may be heated by conveying a gas at a selected temperature on and/or into the tube. The gas may be the same gas used to increase the pressure in the tube. In another embodiment, the tube may be heated by translating a heating element or nozzle adjacent to the tube. In other embodiments, the tube may be heated by the mold. The mold may be heated, for example, by heating elements on, in, and/or adjacent to the mold.

Certain embodiments may include first sealing, blocking, or closing a polymer tube at a distal end. The end may be open in subsequent manufacturing steps. The fluid, (conventionally an inert gas such as air, nitrogen, oxygen, argon, etc.) may then be conveyed into a proximal end of the polymer tube to increase the pressure in the tube. The pressure of the fluid in the tube may act to radially expand the tube.

Additionally, the pressure inside the tube, the tension along the cylindrical axis of the tube, and the temperature of the tube may be maintained above ambient levels for a period of time to allow the polymer tube to be heat set.

Some embodiments provide for heating the tube prior to, during, and/or subsequent to radial expansion. Heating the tube may further induce polymer chain alignment with applied stress. The tube may be heated by any means known to those skilled in the art, for example, by conveying a gas above ambient temperature on and/or into the tube. Once the stent is radially expanded, a stent is fabricated from the polymeric tube. Prior to radial expansion, the stents may be sterilized.

As indicated above, a stent is crimped onto a delivery device so that the stent can be deployed upon insertion at an implant site. The method also includes crimping the stent above ambient temperature. A stent is fabricated from the tube that has been radially expanded by laser cutting or chemically etching a pattern into the polymeric tube.

The method also includes crimping the stent above ambient temperature. Crimping the stent at a temperature above ambient can increase the fracture toughness of the stent. As a result, fractures occurring at crimping or deployment can be reduced or prevented. The stent may be crimped onto a delivery device such as a catheter to form a stent assembly. As discussed above, the brittle nature of polymers and stress and strain on the polymer caused by laser cutting the polymer may result in cracking in a stent during the crimping process an upon deployment. It has been observed that heating the stent to an elevated temperature prior to or during crimping the stent causes the stent to experience less cracking, both when the stent is crimped and when the stent is expanded. Without being limited by theory, heating the stent prior to crimping increases polymer chain mobility and relaxes the chains into a lower energy (less stressed) configuration before crimping the stent. Thus, upon heating the stent prior to or during the crimping process, the stent releases concentrated stress in the stent to prevent strut cracking during crimping or during deployment when the stent is expanded.

Any suitable device can be used to heat the stent, such as an oven, blowing heated gas through the stent, etc. The polymeric stent may be heated for a sufficient period of time of about 2 seconds to about 350 minutes. In some embodiments, the stent is heated for a sufficient time such that the material becomes ductile enough to adequately lower polymer brittleness.

Generally, stent crimping involves affixing the stent to the delivery catheter or delivery balloon such that it remains affixed to the catheter or balloon until the physician desires to deliver the stent at the treatment site. The stent can be crimped by any suitable crimper. Crimpers for crimping medical devices are well known in the art. In one embodiment, the stent is crimped by a sliding wedge crimper. The crimper may be used to crimp the polymer-coated stent onto a delivery device, such as the balloon portion of a catheter. For crimpers such as the sliding wedge crimper, the temperature may be controlled by passage of a stream of dry air, or inert gas through the bore of the catheter. Each wedge of the sliding wedge crimper is heated to the desired temperature. In one embodiment, the stent is pre-heated to a temperature of about 30° C., and the stent is crimped for about 35 seconds by reducing the diameter of the crimper to a diameter of stent of 0.084 inches. In another embodiment, the stent is pre-heated to a temperature of about 30° C. to about 50° C. The stent is then crimped at a temperature of about 30° C. for 130 seconds by crimping the crimper to a diameter of 0.05 inches. In another embodiment, the stent is crimped at a temperature of about 30° C. to about 50° C. The sliding wedge crimper may be heated to any desired elevated temperature. The wedges are then closed to the diameter of the un-crimped stent. In one embodiment, the sliding wedge crimper is heated to a temperature of about 30° C. to 50° C. upon crimping the stent. In another embodiment, the sliding wedge crimper is heated to a temperature of about 30° C. upon crimping the stent.

As mentioned above, the stent may be crimped onto a delivery device to form a stent assembly. The delivery device may be a balloon, or a balloon-catheter assembly. In one embodiment, delivery device is a balloon with a vacuum pump.

In one embodiment, a method for fabricating a stent is disclosed for determining an optimal radial expansion and crimping temperature that corresponds to the least number of fractures in a stent that occur at crimping and deployment. Specifically, the method includes providing multiple lots of two or more polymeric tubes and radially expanding each lot. A lot can include, for example 10 tubes. Each lot is expanded to a different degree of expansion, which can range between, for example, 300% and 800%. In general, a method can include determining the optimal values of one or more fabrication and/or delivery conditions for a polymer stent.

Stents are then fabricated from each of the expanded tubes in the lots. Each lot is then separated into two or more groups. Each group is crimped at a different temperature, between, for example 10° C. and 80° C. The crimped stent is then deployed to a selected diameter. The selected design diameter can correspond to a maximum design diameter, i.e., an implantation diameter. Alternatively, the selected diameter can be greater than the maximum design diameter. An optimal degree of radial expansion and crimping temperature may be determined by observing the number of cracks in each of the stents. The optimal crimping temperature and degree of radial expansion can correspond to the least number of cracks.

In one embodiment, the method of fabricating a stent includes providing multiple lots of tubes and varying at least two conditions during the fabrication of the stents from the tubes. Each stent is then deployed to a selected diameter to determine values of optimal fabrication conditions corresponding to the least number of fractures caused by the deployment of the stents.

Figure 3:
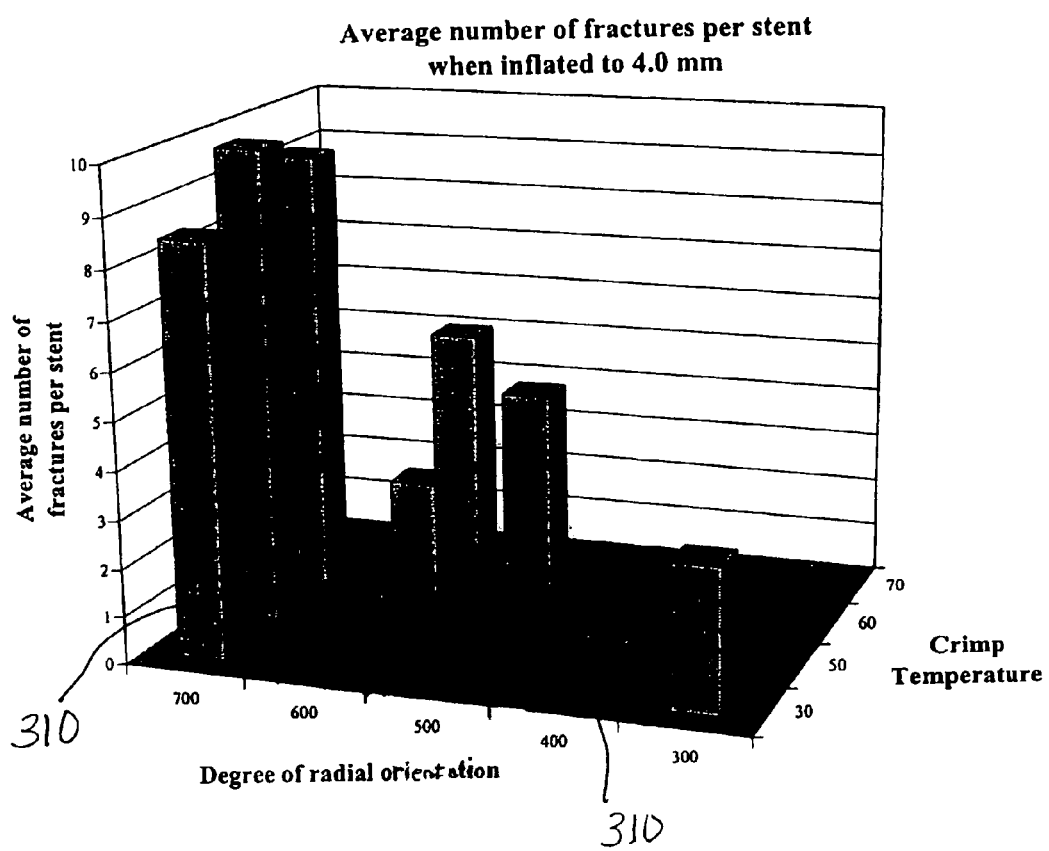
FIG. 3 depicts a chart of the average number of fractures per stent caused by over-expansion of the stents beyond the maximum design diameter.

As depicted by the chart in FIG. 3, optimal fracture toughness may be determined by varying two fabrication conditions in a test of multiple lots of polymeric tubes. FIG. 3 depicts a chart of the average number of fractures per stent in each lot (indicated by the height of the columns) caused by over-expansion of the stents beyond their maximum design diameter. The graph shows the dependence of the average number of fractures per stent versus the degree of radial expansion of tubing verses the crimping temperature. In this particular embodiment, the maximum design diameter of the stents is at 3.25 mm. The stents were over-expanded to a diameter of 4.0 mm.

As depicted in FIG. 3, each lot of 10 polymeric tubes is radially expanded to varying degrees, fabricated into stents, and crimped at various temperatures. Optimal radial expansion degree and optimal stent crimping temperature was then determined by radially expanding the stents to 4.0 mm which is beyond their maximum design diameter. The average number of fractures per stent caused by expanding the stents beyond their maximum design diameter was then recorded, revealing the optimum degree of radial expansion and crimping temperature for the poly(L-lactide) stents. Using such methods, stents having higher fracture toughness may be fabricated.

In one method, each lot of polymeric tubes of two or more samples may be processed with a different value of a selected fabrication condition. For example, if an optimal degree of radial expansion is being tested, each lot has a different degree of radial expansion. Each lot may then be divided into different groups and each group is processed with different crimping temperatures. In one embodiment, one lot, where each lot includes 10 tubes, is radially expanded to 700%, 600%, 500%, 400%, and 300%. The tubes are then fabricated into stents by cutting a stent pattern into each of the tubes. Each lot of stents is then crimped. For example, the lot of tubes that have been radially expanded to 700% is crimped at 30° C., 50° C., 60° C., and 70° C. Tubes that were radially expanded at 300%, 400%, 500%, and 600% are also crimped at such temperatures.

In one embodiment, at least two lots are radially expanding to about 600%, at least two lots are radially expanded to about 500%; and at least two lots are radially expanding to about 400%. The tubes are then laser cut to fabricate a stent from each of the tubes. After forming a stent from each of the tubes, one lot of stents is crimped such that the temperature of the stent is about 30° C. when crimping. Another lot of stents is crimped such that the temperature of the stent is about 50° C. when crimping. The optimal radial-expansion and crimping temperature is then determined as above stents by radially expanding the stents. In one embodiment, the optimal radial expansion and crimping temperature is determined by over-expanding the stents beyond their maximum design diameter. In this way, the relationship between a deformation and fabrication conditions such as crimping temperature is determined. A polymeric tube may be radially expanded by any method known to those skilled in the art, such as blow molding or by use of a cylindrical mold.

Further processing steps in the fabrication of a stent may be included in the embodiments described herein. For example, a radially expanded polymeric tube may be heat set after deformation to allow polymeric chains to rearrange upon deformation. "Heat setting" refers to allowing polymer chains to equilibrate or rearrange to the induced oriented structure, caused by the deformation, at an elevated temperature. During this time period, the polymer in the deformed state may be maintained at an elevated temperature to allow polymer chains to adopt the oriented structure. The polymer may be maintained in the deformed state by maintaining a radial pressure. The polymer tube may then be cooled to a certain temperature either before or after decreasing the pressure. Cooling the tube helps insure that the tube maintains the proper shape, size, and length following its formation. Upon cooling, the deformed tube retains the length and shape imposed by an inner surface of a mold used in the radial expansion.

The method may further include axially extending the polymeric tube prior to or after radially expanding the tube. Other fabrication conditions that can be optimized to obtain desired mechanical behavior such as toughness of the stent, controlled to optimize the mechanical properties of the stent, such as the temperature at which the tube is deformed, strain rate of the deformation (such as axial extension and radial expansion), and time of deformation. The temperature of the tube can be constant during the deformation or be a function of time during the deformation process. Deformation fabrication conditions can also be varied to determine optimal toughness, such as conditions during heat setting of the tube such as the temperature history of the tube during heat setting.

A stent fabricated from embodiments of the stent described herein can be medicated with an active agent. In some embodiments, a coating on the stent may include a drug that can withstand a crimping temperature. A medicated stent may be fabricated by coating the surface of the polymeric scaffolding with a polymeric carrier that includes an active or bioactive agent or drug. An active agent or drug can also be incorporated into the polymeric scaffolding made from the blend.

Additionally, as indicated above, embodiments of the method described herein may be applied to balloon expandable stents, self-expanding stents, stent grafts, and stent-grafts. The stent is used to open a lumen within an organ in a mammal, maintain lumen patency, or reduce the likelihood of narrowing of a lumen.

A stent may be configured to degrade after implantation by fabricating the stent either partially or completely from biodegradable polymers. Polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and may be gradually absorbed and eliminated by the body. Biodegradation refers generally to changes in physical and chemical properties that occur in a polymer upon exposure to bodily fluids as in a vascular environment. The changes in properties may include a decrease in molecular weight, deterioration of mechanical properties, and decrease in mass due to erosion or absorption. Mechanical properties may correspond to strength and modulus of the polymer. Deterioration of the mechanical properties of the polymer decreases the ability of a stent, for example, to provide mechanical support in a vessel.

As mentioned above, the stent may be made from a polymer that is biostable, biodegradable, or a combination thereof. For example, the polymer may be selected from the group consisting essentially of poly(D,L-lactide); poly(L-lactide); poly(L-lactide-co-glycolide); or poly (D,L-lactide-co-glycolide). Other representative examples of polymers that may be used to fabricate a stent coating include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(L-lactide-co-ε-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating a stent according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. The stents may also be metallic; low-ferromagnetic; non-ferromagnetic; biostable polymeric; biodegradable polymeric or biodegradable metallic.

While particular embodiments of the present invention have been shown and described, it will be obvious to those skilled in the art that changes and modifications can be made without departing from this invention in its broader aspects.

The invention claimed is:

1. A method of fabricating a stent to have a reduced number of cracks when expanded from a crimped configuration to an expanded configuration, comprising:
   (a) selecting a degree of radial expansion from a plurality of radial expansion amounts ranging between 100% and 800% and selecting a crimping temperature from a plurality of crimping temperatures ranging between 10 degrees and 80 degrees Celsius;
   (b) radially expanding a polymer tube by the selected degree of radial expansion;
   (c) forming the stent from the radially expanded tube;
   (d) crimping the stent at the selected crimping temperature;
   (e) balloon expanding the stent from its crimped configuration to an expanded configuration; and
   (f) repeating steps (b) through (e) for at least four different combinations of at least two different degrees of radial expansion and at least two different crimping temperatures; and
   fabricating the stent using a combination of radial expansion and crimping temperature, selected from among the at least four different combinations, that produced the fewest number of cracks in the expanded stent.

2. The method according to claim 1, wherein the polymeric tube comprises a biostable polymer, biodegradable polymer, or a combination thereof.

3. The method according to claim 1, wherein the polymeric tube consists essentially of poly(L-lactide).

4. The method of claim 1, wherein the stent is fabricated using a radial expansion between about 400% to 600% and a crimping temperature between about 30° C. to 50° C.

5. The method of claim 1, wherein step (f) is repeating steps (b) through (e) for at least twenty five different combinations of degrees of radial expansion and crimping temperatures.

6. The method of claim 5, wherein the selected radial expansion amounts are 700%, 600%, 500%, 400% and 300% and the selected crimping temperatures are 30° C., 50° C., 60° C. and 70° C.

7. The method of claim 1, wherein the selected radial expansion amounts are 400% and 500% and the selected crimping temperatures are 30° C. and 50° C.

8. A method of fabricating a stent to have a reduced number of cracks when expanded from a crimped configuration to an expanded configuration, comprising:
   selecting a first radial expansion amount and a second radial expansion amount, each radial expansion amount being between 100% and 800%;
   selecting a first crimping temperature and a second crimping temperature, each crimping temperature being between 10 degrees and 80 degrees Celsius;
   forming, crimping and then expanding a first and second plurality of stents, wherein the first plurality of stents is formed using the first radial expansion amount and crimped using the first crimping temperature and the second plurality of stents is formed using the first radial expansion amount and crimped using the second crimping temperature;

forming, crimping and then expanding a third and fourth plurality of stents, wherein the third plurality of stents is formed using the second radial expansion amount and crimped using the first crimping temperature and the fourth plurality of stents is formed using the second radial expansion amount and crimped using the second crimping temperature; and fabricating the stent using a combination of radial expansion amount and crimping temperature based on the number of cracks that appeared in each of the first, second, third and fourth plurality of stents.

* * * * *